US008682953B2

(12) United States Patent
Wedel

(10) Patent No.: US 8,682,953 B2
(45) Date of Patent: Mar. 25, 2014

(54) HOSPITAL SYSTEM

(75) Inventor: Matthias Wedel, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 473 days.

(21) Appl. No.: 11/994,610

(22) PCT Filed: Jun. 30, 2006

(86) PCT No.: PCT/EP2006/063749
§ 371 (c)(1),
(2), (4) Date: Jul. 25, 2008

(87) PCT Pub. No.: WO2007/006667
PCT Pub. Date: Jan. 18, 2007

(65) Prior Publication Data
US 2008/0292156 A1 Nov. 27, 2008

(30) Foreign Application Priority Data
Jul. 7, 2005 (DE) .......................... 10 2005 031 894

(51) Int. Cl.
*G06F 15/16* (2006.01)

(52) U.S. Cl.
USPC .......................................................... 709/201

(58) Field of Classification Search
USPC .......................................................... 709/201
See application file for complete search history.

(56) References Cited

U.S. PATENT DOCUMENTS

| 6,263,330 | B1 | 7/2001 | Bessette |
| 6,348,793 | B1 * | 2/2002 | Balloni et al. ................ 324/309 |
| 6,529,757 | B1 | 3/2003 | Patel et al. |
| 6,718,192 | B1 * | 4/2004 | Samara et al. ................ 600/407 |
| 2004/0230613 | A1 | 11/2004 | Goldstein et al. |
| 2005/0025349 | A1 | 2/2005 | Crewe |
| 2005/0080330 | A1 | 4/2005 | Masuzawa et al. |
| 2005/0110788 | A1 | 5/2005 | Turner et al. |
| 2006/0056680 | A1 | 3/2006 | Stutsman et al. |
| 2006/0269106 | A1 * | 11/2006 | Staring et al. ................ 382/128 |

FOREIGN PATENT DOCUMENTS

| DE | 196 25 834 A1 | 1/1998 |
| DE | 103 09 165 A1 | 9/2004 |
| DE | 20 2004 016 492 U1 | 12/2004 |

OTHER PUBLICATIONS

Written Opinion (with translation).
German Office Action (with translation) dated Dec. 23, 2005.
International Search Report.

* cited by examiner

*Primary Examiner* — Noel Beharry
*Assistant Examiner* — Farhad Ali
(74) *Attorney, Agent, or Firm* — Lempia Summerfield Katz LLC

(57) ABSTRACT

A hospital system for generating image data is provided. The Hospital System includes a module for determining raw image data, with a server that is spatially separated from the module and can calculate image data from the raw image data, and a network for transmitting the raw image data from the module to the server. The hospital system may include a number of modules.

16 Claims, 1 Drawing Sheet

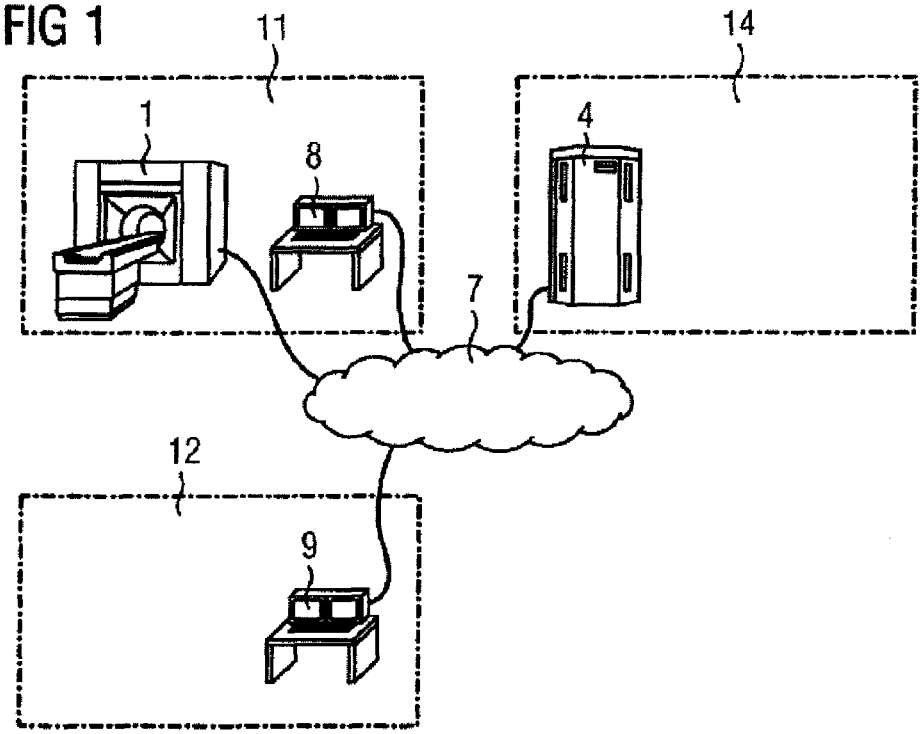
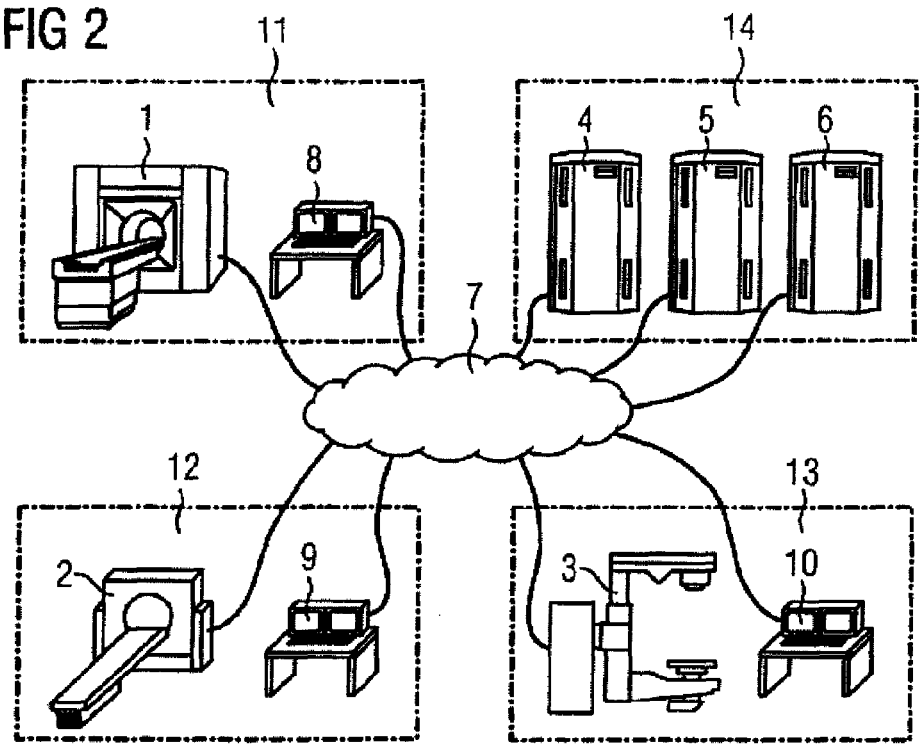

HOSPITAL SYSTEM

The present patent document claims the benefit of PCT Application Serial Number PCT/EP2006/063749, filed Jun. 30, 2006, designating the United States, and claims benefit of DE 10 2005 031 894.0, filed Jul. 7, 2005, both of which are hereby incorporated by reference.

BACKGROUND

The present embodiments relate to a hospital system that generates image data with the collaboration of at least one modality.

Modalities, such as X-ray tomographs, MRI scanners, C-arm X-ray systems, or other imaging systems, generate images of a patient that are relevant to diagnosis. For archiving these digital image data, picture archiving and communications systems (PACS) are often employed.

The modalities typically include a sensor system component with a data processor, which together generate raw image data of an examined area of the patient; a computer unit, which, from the raw image data, calculates finished image data; and optionally a further computer unit for user operation of the applicable modality and for displaying the calculated image data. Modalities may be connected via an interface with a network. The image data may be transmitted, for example, to a PACS system via the network Access to the image data stored in the PACS system can then be gained via the network from various workstations distributed around the hospital.

The modalities generate waste heat because the modalities have many system components, each of which consume electrical energy that may have to be dissipated with noisy fans. This waste heat heats up the room in which the modality is located. This leads to stress in terms of noise and waste heat for both the patient and the person operating the particular modality. The waste heat can be dissipated from the applicable room using a ventilation or air conditioning system. Moreover, the many system components of a modality makes for high procurement costs for the modality.

SUMMARY AND DESCRIPTION

The present embodiments may obviate one or more of the drawbacks or limitations inherent in the related art. For example, in one embodiment, a hospital system i generates image data using a modality that is integrated with the hospital system.

In one embodiment, a hospital system for generating medical image data includes a modality that generates raw image data, a server that is spatially separated (remotely located) from the modality, and a network that transmits the raw image data from the modality to the server. The server can calculate image data from the raw image data and simulate one virtual machine per modality for the calculation of the image data from the raw image data by the respective modality.

A computer unit in the immediate vicinity of the modality may be removed because of the spatial separation of the modality for ascertaining the raw image data and the server for calculating the image data from the raw image data.

A network, which often already exists, may be used to transmit the raw image data from the modality to the server. Especially in the case of 3D measurement data of an X-ray tomograph or a MRI scanner, the reconstruction of the image data from the raw image data measured by the applicable modality is computer-intensive and generates a great deal of waste heat. Replacing a computer unit, disposed at the modality that calculates the image data with a server that is spatially separate from the modality moreover makes it economically possible to speed up the calculation retroactively by replacing the server with a more-powerful server, without replacing the modality itself. The term "server" may include more than one server.

A plurality of modalities may be integrated with the hospital system. This may reduce the procurement costs per modality, since one separate computer unit per modality can be dispensed with. Until now, the computer units of the modalities were only ever used when raw image data was generated at the applicable modality. Better utilization by the modalities of the server than of the separate computer units is now possible. The full computer power of the server is usually available for calculating the various image data from the raw image data because raw data is rarely present from different modalities at the same time.

In one embodiment, the hospital system includes a plurality of redundantly designed servers. The image data can be successfully calculated from the raw image data even if one or more of the servers fails, so that higher fail-safeness of the hospital system is ensured. During maintenance work on one of the servers, there are no downtimes in which it is not possible to calculate the image data. The hospital system is easily scalable, in terms of its computation power, by adding a further server.

The servers may be disposed in one central control. Only the central control is burdened with waste heat or noise from the servers. In the central control, all the servers may be cooled or ventilated jointly. For maintenance purposes, the servers are easily accessible jointly in one room.

In one embodiment, one virtual machine per modality for the calculation of the image data from the raw image data by the respective modality can be simulated. Each virtual machine takes on the function of a computer unit disposed at the modality, so that the raw image data or image data processing can be adopted.

Using the virtual machines, it is possible to calculate the image data independently for each modality, without mutual interference among various programs for calculating the image data. Various operating systems can also be installed on the virtual machines.

In one embodiment, the servers may further process the image data using computation-intensive methods, for example, computer-aided diagnosis (CAD). The server may calculate the image data and provide computer-supported aid in diagnosis with little waste heat or noise at the applicable modality. The methods known from CAD include, for example, the computer-supported detection of tumors in the image data.

Using a data link of the server with a PACS system for storing the image data in memory, the calculated image data may be archived. The image data may be automatically stored in the PACS system. The image data archived in the PACS system is accessible, for example, using a workstation connected to the network.

The PACS system may be integrated with the server. An additional server for the PACS system may be avoided. The PACS system of the server may be jointly used for calculating the image data from the raw image data. Dual storage of the image data on the server and in a separate PACS system can be avoided, along with an additional transmission of data from the server to the PACS system. If a plurality of servers are provided in the hospital system, the PACS system can be integrated with one of the servers, for example.

In one embodiment, the server may perform other functions of the PACS system for the image data, for example, computation-intensive procedures. The server may also store the image data. The other functions of the PACS system include, for example, encoding and decoding of the image data, distributing the image data to the workstation, and searching the image data in the PACS system.

A workstation, disposed at the modality, that displays the image data may be accessible via the network. The workstation may display of the image data, which was calculated by a server that is spatially separate from the modality, at the modality. This makes quality control of the image data shortly after the raw image data has been generated by the modality possible, so that the raw image data can be re-ascertained if necessary. The workstation may be a thin client. The thin client produces little waste heat or noise compared to the normal workstation. The thin client requires less power than a normal workstation and fewer computer components. The majority of the computation work is taken over by the server, with which the thin client is connected via the network. The image data that can be displayed with the aid of the workstation can be called up, for example, in an uncomplicated way, from the PACS system via the network. Optionally, even previously archived image data can be called up by the workstation for comparison with the currently stored image data.

The workstation is also intended for user operation of the modality. User operation includes, among other tasks, setting the parameters for ascertaining the raw image data, and starting the ascertainment of the raw image data.

BRIEF DESCRIPTION OF THE DRAWINGS

FIG. 1 shows a hospital system having a modality that is connected via a network to a server in another room; and FIG. 2 shows a hospital system having three modalities, each disposed in separate rooms.

DETAILED DESCRIPTION

In one embodiment, as shown in FIG. 1, a modality, such as a MRI scanner 1, is disposed in a room 11. The MRI scanner 1 is connected via a network 7 to a server 4 disposed in another room 14. The various sets of raw image data ascertained (generated) by the MRI scanner 1 can be transmitted via the network 7 from the MRI scanner 1 to the server 4. The server 4 can calculate the image data from the raw image data. With the aid of the server 4, sectional view or 3D views, for instance, of a patient being examined using the MRI scanner 1 can be calculated.

A hospital (medical facility) system may include a workstation 8 at the MRI scanner 1 and a further workstation 9 in a separate room 12. The workstations 8, 9 display the image data calculated using the server 4. The calculated image data is accessible via the network by the respective workstations 8 and 9. A user of the MRI scanner 1, for example, can check for successful performance of MRI scanning at the workstation 8 disposed in the same room 11, or a physician at the workstation 9 in the separate room 12 can make a diagnosis based on the displayed image data. The workstations 8, 9 may be thin clients. A thin client has data input and output, while most of the data processing is done in the server 4 using the display of the image data. In this exemplary embodiment, the predominant portion of computation work is shifted from the MRI scanner 1 and the workstation 8 to the spatially separate server 4. The waste heat and noise burden on the room 11 from the MRI scanner 1 and the workstation 8 is reduced.

A PACS system is integrated with the server 4. The PACS system automatically stores the sets of image data each calculated by the server 4 in memory. Via the network 7, the PACS system is accessible by the workstations 8, 9. Besides the current image data at the time, even image data stored in the PACS system previously can be accessed.

In one embodiment, as shown in FIG. 2, a hospital system may include three modalities 1-3, each disposed in a different room 11-13. The modalities may include a MRI scanner 1, an X-ray CT scanner 2, and a U-arch X-ray system 3. Each modality may be connected via the network 7 to one of three redundantly designed servers 4-6 in a further room 14. The further room may be a central control. The raw image data ascertained by each of the modalities 1-3 can be transmitted via the network 7 to at least one of the servers 4-6. The at least one of the servers 4-6 can calculate the image data from the raw image data. The calculations required in each case are distributed among the servers 4-6 in such a way that the servers carry as uniform a load as possible. If of the three servers 4-6 should be unavailable at the moment for calculating the image data, for example, because of a defect or because of maintenance work, then because of the redundance of the servers, the image data calculation can be shifted to the remaining servers. The servers 4-6 are jointly disposed in the central control. The central control is the only room burdened by the waste heat or the noise generated by the servers 4-6. Since only in exceptional cases do the servers 4-6 have to calculate image data from more than one modality 1-3 simultaneously, the full computation power of the servers 4-6 is available to each of the modalities 1-3 for calculating the image data. This synergistic effect allows easy scalability of the hospital system, by adding further modalities.

In one embodiment, the servers 4-6 simulate one virtual machine per modality 1-3. The servers 4-6 take over the function of a computer unit for calculating the image data that in the prior art was integrated with the respective modality. This includes three workstations 8-10, each disposed at a respective one of the three modalities 1-3, and the workstations are each connected to the servers 4-6 via the network 7. The workstations 8-10 are intended for displaying the image data that is accessible via the network 7.

The present embodiments relate to a hospital system for generating medical image data. The hospital system includes: a modality for ascertaining raw image data; a server, spatially separated from the modality, for calculating image data from the raw image data; and a network for transmitting the raw image data from the modality to the server. The hospital system may reduce the waste heat produced in the generation of the image data at the modality, and the noise produced in dissipating this waste heat. The hospital system may include a plurality of modalities. A synergistic effect is furthermore attained, which in particular reduces costs, compared to a typical hospital system that has a plurality of modalities that each have their own computer unit for ascertaining the image data from the raw image data.

The invention claimed is:

1. A hospital system for generating medical image data, the hospital system comprising:
   a plurality of imaging modalities disposed in a plurality of rooms, each imaging modality of the plurality of imaging modalities configured to generate raw image data;
   a plurality of servers disposed in a central control room spatially separated from the plurality of rooms, each server of the plurality of servers configured to calculate image data from the raw image data and simulate a virtual machine for each imaging modality of the plurality of imaging modalities for the calculation of the image data from the raw image data generated by the respective modality, each of the virtual machines being tailored to a specific imaging modality of the plurality of imaging modalities;

a network that transmits the raw image data from the plurality of imaging modalities to the plurality of servers; and a workstation configured to display the image data that is accessible via the network, wherein the virtual machines are configured to calculate the image data independently for each imaging modality of the plurality of imaging modalities, wherein the workstation is a thin client, and wherein the plurality of imaging modalities includes an X-ray tomography device, an MRI scanner, a C-arm X-ray system, or an imaging system.

2. The hospital system as defined by claim 1, wherein the plurality of servers comprises redundantly designed servers.

3. The hospital system as defined by claim 1, wherein the plurality of servers processes the image data using computer-aided diagnosis.

4. The hospital system as defined by claim 3, wherein the plurality of servers comprises redundantly designed servers.

5. The hospital system as defined by claim 1, wherein the plurality of servers is linked with a picture archiving and communications system (PACS) for storage of the image data in a memory of the PACS.

6. The hospital system as defined by claim 5, wherein the PACS is integrated with one server of the plurality of servers.

7. The hospital system as defined by claim 6, wherein the plurality of servers is operative to perform the functions of the PACS to the image data.

8. The hospital system as defined by claim 5, wherein the image data is automatically stored in the PACS.

9. The hospital system as defined by claim 1, wherein the workstation is disposed at one imaging modality of the plurality of imaging modalities, and wherein the one imaging modality of the plurality of imaging modalities is operative to be controlled by the workstation disposed at the one imaging modality of the plurality of imaging modalities.

10. The hospital system as defined by claim 1, wherein the workstation is disposed at one imaging modality of the plurality of imaging modalities.

11. The hospital system as defined by claim 1, wherein the plurality of imaging modalities includes at least two imaging modalities of an X-ray tomography device, an MRI scanner, a C-arm X-ray system, and an imaging system.

12. The hospital system as defined by claim 1, further comprising a plurality of workstations, each workstation of the plurality of workstations disposed at a respective one of the plurality of imaging modalities, the plurality of workstations comprising the workstation.

13. The hospital system as defined by claim 12, wherein each workstation of the plurality of workstations is connected to each server of the plurality of servers via the network.

14. An imaging system for use in a medical facility, the imaging system comprising:

a plurality of imaging devices disposed in a plurality of rooms, each imaging device of the plurality of imaging devices configured to generate raw image data, a thin client disposed near one imaging device of the plurality of imaging devices, a plurality of servers disposed in a central control room located remotely from the plurality of the rooms and the thin client, the plurality of servers configured to calculate image data from the raw image data provide processing for the thin client, and simulate a virtual machine for each imaging device of the plurality of imaging devices for the calculation of the image data from the raw image data generated by the respective imaging device, each of the virtual machines being tailored to a specific imaging device of the plurality of imaging devices, and a network that is operative to transmit the raw image data from the plurality of imaging devices to the plurality of servers, wherein the plurality of servers is configured to calculate the image data independently for each imaging device of the plurality of imaging devices, and wherein the plurality of imaging devices includes an X-ray tomography device, an MRI scanner, a C-arm X-ray system, or an imaging system.

15. A hospital system for generating medical image data, the hospital system comprising:

a plurality of imaging systems, each imaging system of the plurality of imaging systems comprising an imaging modality that generates raw image data and a thin client disposed at and configured to control the imaging modality, the plurality of imaging systems being disposed in a plurality of rooms, a server disposed in a room spatially separated from the plurality of imaging systems, the server configured to calculate image data from the raw image data and simulate a virtual machine for the calculation of the image data from the raw image data for each imaging system of the plurality of imaging systems, each of the virtual machines being tailored to a specific one of the imaging modalities, a network that transmits the raw image data from the plurality of imaging systems to the server and transmits the image data for each respective imaging system from the server to a display of the thin client of the respective imaging system, wherein a majority of the processing for creating an image on the display from the raw image data is performed by the server and not the respective imaging system, wherein the virtual machines are configured to calculate the image data independently for each imaging system of the plurality of imaging systems, and wherein the imaging modalities include an X-ray tomography device, an MRI scanner, a C-arm X-ray system, or an imaging system.

16. The hospital system as defined by claim 14, further comprising a thin client disposed near each imaging device of the plurality of imaging devices, wherein the plurality of servers is configured to provide processing for each of the thin clients.

\* \* \* \* \*